United States Patent
Chabot

(10) Patent No.: US 8,721,986 B2
(45) Date of Patent: May 13, 2014

(54) FRESHENING CLIP CABIN AIR CLEANER

(75) Inventor: Holly S. Chabot, Troy, MI (US)

(73) Assignee: Mann+Hummel GmbH, Ludwigsburg (DE)

( * ) Notice: Subject to any disclaimer, the term of this patent is extended or adjusted under 35 U.S.C. 154(b) by 292 days.

(21) Appl. No.: 13/228,721

(22) Filed: Sep. 9, 2011

(65) Prior Publication Data

US 2013/0064721 A1 Mar. 14, 2013

(51) Int. Cl.
- *A61L 2/00* (2006.01)
- *B01D 53/02* (2006.01)
- *B01D 50/00* (2006.01)
- *B01D 46/02* (2006.01)

(52) U.S. Cl.
USPC .............. 422/300; 55/315; 55/341.1; 96/108; 96/222

(58) Field of Classification Search
USPC ................ 422/5, 560, 123, 300, 203; 55/315, 55/341.1, 410, 434, 482, DIG. 45; 96/108, 96/222
See application file for complete search history.

(56) References Cited

U.S. PATENT DOCUMENTS

| | | |
|---|---|---|
| 5,407,642 A | 4/1995 | Lord |
| 5,478,505 A | 12/1995 | Warner et al. |
| 5,527,493 A | 6/1996 | Warner et al. |
| 6,123,906 A | 9/2000 | Farmer |
| 6,197,263 B1 | 3/2001 | Blount |
| 7,753,982 B2 * | 7/2010 | Merritt ............................ 55/502 |
| 7,770,817 B2 | 8/2010 | Macor |
| 2010/0219199 A1 | 9/2010 | Andochick |

* cited by examiner

*Primary Examiner* — Monzer R Chorbaji
(74) *Attorney, Agent, or Firm* — James Hasselbeck

(57) ABSTRACT

A freshening clip cabin air cleaner includes an airflow permeable filter media arranged in and supported in an annular frame member. Support members may be provided at one or both airflow face of the filter media and includes an elongated clip mounting means mounting the freshening clip cabin air cleaner to the air vent grill. A scented air freshening material having volatizing aromatic agents is arranged on or in at least one of the support members, the annular frame or the filter media.

17 Claims, 3 Drawing Sheets

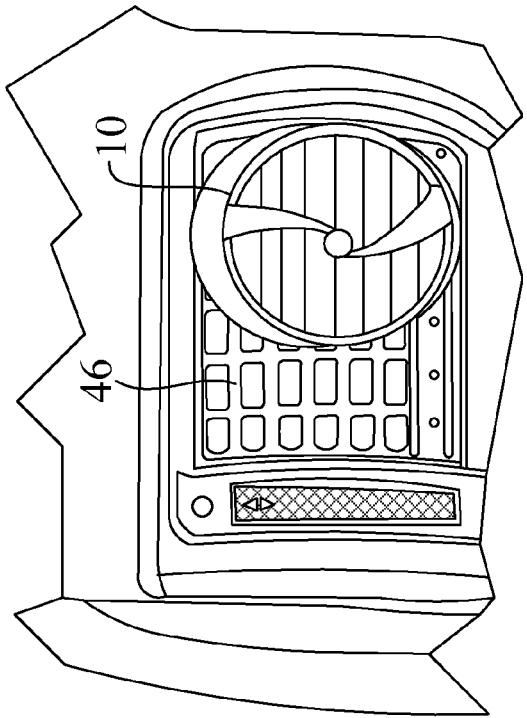
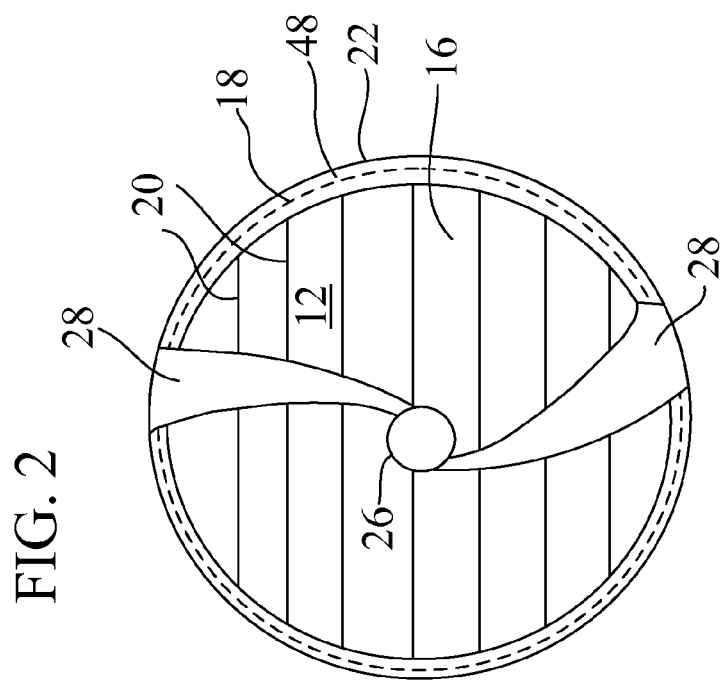

FRESHENING CLIP CABIN AIR CLEANER

TECHNICAL FIELD

The invention relates to air filtering and air freshening devices and, more particularly, to an air freshening clip cabin air cleaner including an air filter device with an integrated air freshening agent detachably mounted to a motor vehicle interior air ventilation duct opening for filtering and freshening the vehicle cabin air.

BACKGROUND OF THE INVENTION

Air fresheners are known for use in motor vehicle passenger cabins. One often seen variety includes the air freshener "trees" that may be observed hanging from a vehicle inside mirror.

The air freshening agent may be provided as a solid, liquid or gel material. In the case of liquids, the liquid may be provided in a bottle with a wick to volatize the freshening agent into the air, alternately liquids may be saturated into or absorbed into sponge, cloth or foam carrier materials from which components of the freshener liquid volatize or evaporate into the air.

U.S. Pat. No. 5,407,642 discloses a clip mounted air freshener assembly having a holder into which an air freshening element is inserted.

U.S. Pat. No. 6,123,906 discloses a unitary fork-shaped air freshener of impregnated polypropylene material and insertable into an air vent discharge.

U.S. Pat. No. 6,1976,263 discloses an electrically heated air freshener for automobiles, wherein the fragrance dispensing unit includes electrical heating elements heating replaceable gel-scent cartridges and an electrical plug for receiving electrical power from a cigarette lighter socket.

It is also known to be advantageous to provide air filter elements (also known as cabin air filters) arranged within and integrated within the passenger compartment air ventilation duct system of a motor vehicle to remove various types of particulate contaminants. While some vehicles are manufactured and equipped with cabin air filters, a greater number of motor vehicles lack provisions for or to install a cabin air filter in the motor vehicle. In such vehicles it is at least difficult and maybe nearly impossible to retrofit a cabin air filter into the air ventilation duct system to provide cabin air filtration.

Therefore there remains a need in the art for an air freshening clip cabin air cleaning device including an air filter device with an integrated air freshening agent which is low in cost and easily installed into or onto the air ventilation outlet grill, which is adapted to filter at least a portion of the air ventilation duct airflow while providing an aromatic air freshening agent to diffuse a pleasant scent into the air.

SUMMARY OF THE INVENTION

According to various aspects of the invention, a freshening clip cabin air cleaner includes an airflow permeable filter media, an annular frame member arranged at and extending circumferentially around the peripheral edges of the filter media providing support to the filter media. At least one support member is arranged at and extends over at least a portion of the airflow faces of the filter media and retaining the filter media within the annular frame. An elongated clip mounting means has a first end mounted to at least one of the support members and extends axially outwardly away from the filter media. The elongated clip means has an end detachably mountably engaged into an air vent grill to detachably mount the freshening clip cabin air cleaner to the air vent grill. An scented air freshening material including volatizing aromatic agents is arranged on or in at least one of the support members or the annular frame member or the filter media where the freshening material may be volatized by the air vent airflow to scent the air. At least one of the annular frame and/or the support member(s) retains the filter media within the annular frame member.

According to another aspect of the invention, the support members include a front support member arranged on the outlet airflow face, the front support member including a centrally arranged mounting hub arranged at the outlet airflow face having a hole extending therethrough and a plurality of shaped elongated wing members having a first end permanently affixed to the hub and extending radially outwardly from the hub and an opposing second end with the wing members extending across a portion of the outlet face. The front support member is a unitary one-piece component. The first end of the clip mounting means extends through the hole in the filter media and therefrom through the hole in the front support member.

According to another aspect of the invention, the support members include a rear support member arranged on the inlet airflow face. The rear support member includes a centrally arranged mounting hub arranged at the inlet airflow face having a hole extending therethrough and a plurality of shaped elongated wing members having a first end permanently affixed to the hub and extending radially outwardly from the hub and to an opposing second end. The wing members extending across a portion of the inlet face. The rear support member is a unitary one-piece component. The first end of the clip mounting means is received through the hole in the rear support member, extending therefrom through the hole in the filter media.

According to another aspect of the invention, the annular frame member is circumferentially closed with the annular frame member encircling and enclosing all of the peripheral outside edges of the filter media.

According to another aspect of the invention, the at least one support member is a unitary one-piece component with the annular frame member.

According to another aspect of the invention, the elongated clip means includes an elongated mounting member having a first and a second elongated mounting rod members positioned in a side-by-side substantially parallel arrangement. The mounting rod members include a cooperatively engaging retention feature formed onto or into the mounting rod members. The retention feature is configured to detachably mount the air freshening filter to the air vent grill.

According to another aspect of the invention, the annular frame member has a generally "U" shaped cross section defined by two spaced legs and a connecting outer wall with a gap between the legs. The peripheral filter media edges are received in the "U" shaped gap. One of the legs extends inwardly from the peripheral filter media edges to cover an outer portion of the filter media inlet face and another one of the legs extends inwardly from the peripheral filter media edges to cover an outer potion of the filter media outlet face.

According to another aspect of the invention, the support members are substantially rigid.

According to another aspect of the invention, the wing members extending across the portion of the outlet face abut against the annular frame member.

BRIEF DESCRIPTION OF THE DRAWINGS

The accompanying Figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

Features of the present invention, which are believed to be novel, are set forth in the drawings and more particularly in the appended claims. The invention, together with the further objects and advantages thereof, may be best understood with reference to the following description, taken in conjunction with the accompanying drawings. The drawings show a form of the invention that is presently preferred; however, the invention is not limited to the precise arrangement shown in the drawings.

FIG. 2 depicts a schematic view of the outlet airflow face of the air freshening clip cabin air cleaning device of the above Figures, showing the filter media and an embodiment of the swept decorative front support member, consistent with the present invention; and FIG. 3 depicts an embodiment of the air freshening clip cabin air cleaning device detachably mounted onto the air vent grill.

Figure 1A:
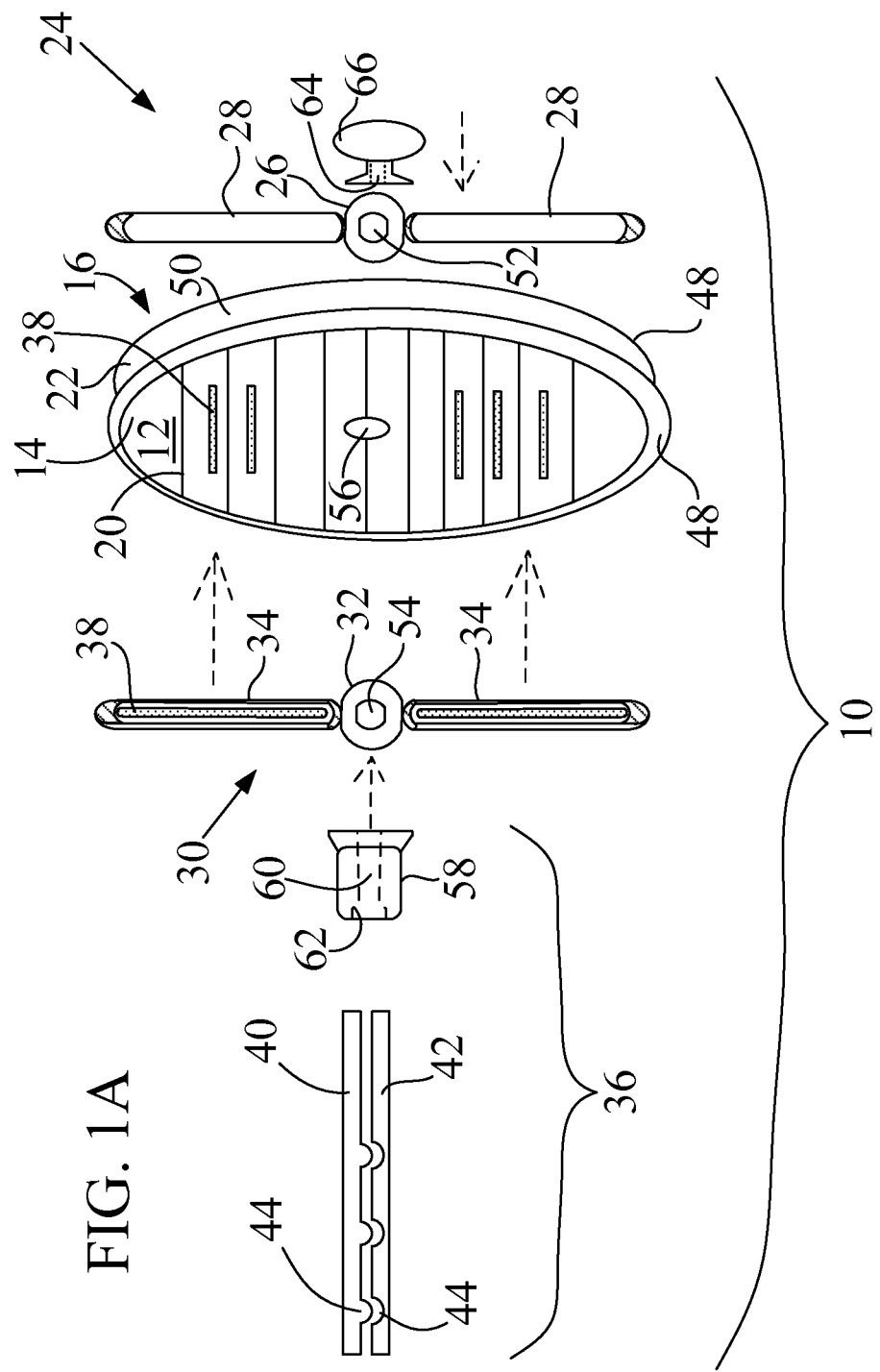
FIG. 1A depicts an exploded schematic assembly view of an air freshening clip cabin air cleaning device, consistent with the present invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

Before describing in detail embodiments that are in accordance with the present invention, it should be observed that the embodiments reside primarily in combinations of apparatus components related to an air freshening clip cabin air cleaning device. Accordingly, the apparatus components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

In this document, relational terms such as first and second, top and bottom, and the like may be used solely to distinguish one entity or action from another entity or action without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

FIG. 1A depicts an exploded schematic assembly view of a freshening clip cabin air cleaner 10 consistent with the present inventive disclosure. An air permeable filter media 12 is arranged in and has peripheral edges 18 contained or enclosed within a supportive and preferably substantially rigid annular frame member 22. The frame member 22 is preferably circumferentially closed and preferably extends completely around the peripheral edges 18 of the filter media 12.

The air permeable filter media 12 may be realized as any variety of filtering media operable to remove contaminants and/or particulates from air, including synthetic non-woven media, cellulose based or paper filter media and/or foam filtering media, for some examples. In the present invention a synthetic non-woven fabric media is preferred. The non-woven filter media may be sheet which is pleated, or preferably is a non-pleated filter mat of synthetic non-woven filter media. Preferably the non-pleated filter mat is thicker than a pleated paper media, but prefereably is also less dense providing even greater porosity for air flow at a lower pressure drop than in paper filter media. In other embodiments the filter media may be pleated or unpleated media such as: paper filter media, woven fabric media or porous foam media, or combinations of any the media types listed herein. Other types of filter media may also be utilized as are known to those skilled in the art.

As is known to those skilled in the art, a pleated filter media is formed by folding a filter media sheet at a plurality of spaced and generally parallel fold lines to provide a zigzag or accordion shaped filter media.

Preferably the air permeable filter media 12 is secured to the interior of the annular frame member 22, such as by, for example, an adhesive so as to permanently affix the filter media 12 to the annular frame member.

In other embodiments it may be desirable to enclose the filter media 12 about its peripheral edges 18 within the annular frame member 22 without use of an adhesive.

Preferably, although not required, the annular frame member has a "U" shaped cross section defined by two spaced legs 48 positioned in a side-by-side spaced parallel relationship. The legs are connected at their radially outer edges by a connecting outer wall 50, which generally abuts the peripheral filter media edges 18 of the filter media 12. Radial outer edge portions of the filter media 12 are received within the gap formed between the spaced legs of the "U" shaped cross section such that respective ones of the legs extend over the peripheral media edges 18 of the filter media 12 and onto the circumferential outer portion of the inlet airflow face 14 or outlet airflow face 16 of the filter media 12.

Regardless of whether the filter media 12 is adhesively secured to the annular frame member 22 or is only captured or retained between the spaced legs 48 of the annular frame member 22, it is highly preferable that the filter media 12 and annular frame member 22 form a substantially unitary component, which is to say that the filter media 12 is reliably captured within the annular frame member 22 and held in place by the support members 24, 30, if present, so the filter media 12 does not become dislodged from the annular frame member 22 during use.

The air permeable filter media 12 has an inlet airflow face 14 generally facing the out of the air vent on which the freshening clip cabin air cleaner air 10 is installed and an opposing outlet air face 16 generally facing away from the air vent and (when installed in an motor vehicle) into the interior of the motor vehicle.

It is preferable to provide additional support to the filter media 12 to maintain it securely within the annular frame member 22 during use. To that end a front support member 24 may be arranged on the outlet airflow face 16 of the filter media. Similarly, a rear support member 30 may be arranged at the inlet airflow face 14 of the filter media 12. Preferably the support members 24, 30 extend fully across a portion of the airflow face 14,16 onto which they are arranged. Even more preferably, the support members 24, 30 extend radially outwardly to abut against and/or press against the annular frame member 22. In the case of a "U" shaped annular frame member, each support member 24, 30 extends radially outwardly to abut against and/or press against the outer surface of a respective one of the spaced legs 48 of the annular frame member 22.

In some embodiments, the support members 24, 30 are separate components from the annular frame member 22. In other embodiments, one or both of the support members 24, 30 may be permanently and non-removeably affixed to the annular frame member so as to form a unitary one-piece component which is exchanged or replaced as a unit.

Preferably each support member 24, 30 has the following general features. The central portion of the support member 24, 30 includes a mounting hub 26, 32 having a hole 52, 54 extending therethrough. The hub 26, 32 is arranged against or onto a central portion of the filter media airflow face 14, 16. A complimentary aligned hole 56 is provided in the filter media 12 extending between the inlet airflow face 14 and the outlet airflow face 16. An end of an elongated clip means 36 is received through the hole 54 of the rear support member 30 mounting hub 32, then through the hole 56 of the filter media to continue into and through the hole 52 of the front support member 24 mounting hub 26, then extending into and detachably mounting into the receiving hole 64 of the brand circle clip 66. The brand circle clip 66 captures and secures the clip means 36 to the brand circle clip 66, thereby affixing the filter media 12, annular frame member 22 and support members 24, 30 onto the clip means 36. The brand circle clip preferably has a substantially flat outer face onto which a product brand symbol or trademark is arranged.

In the clip means embodiment shown in FIG. 1A, the elongated clip means 36 includes spaced rod members 40, 42 positioned in a side-by-side substantially parallel arrangement. The rod members 40, 42 each have an end received into and extending through the hole 60 of the rod-tensioning member 58. Preferably the rod tension member 58 is made of an elastomeric material such that the rod tension member 58 may act to compress or squeeze the rod members 40,42 together such that the rod members 40,42 are operable to compressibly grip and detachably mount the air freshening filter 10 into a vent grill of an air vent.

The rod members 40,42 may be comprised of a deflectable or elastic material such that they may be deflected apart and then compressibly grip a portion of the air vent grill between the rod members 40, 42, even if the rod-tensioning member 58 is realized with as inelastic material.

The rod tensioning member 58 includes a tapered entrance 62 to the rod tensioning member hole 58 to aid in insertion of the rod members 40, 42 through the rod tensioning member hole 58 and to aid in spreading or expanding the rod tensioning member hole 58 and/or compressing the rod member 40, 42, especially in the case of an elastomeric rod tensioning member 58.

Figure 1B:
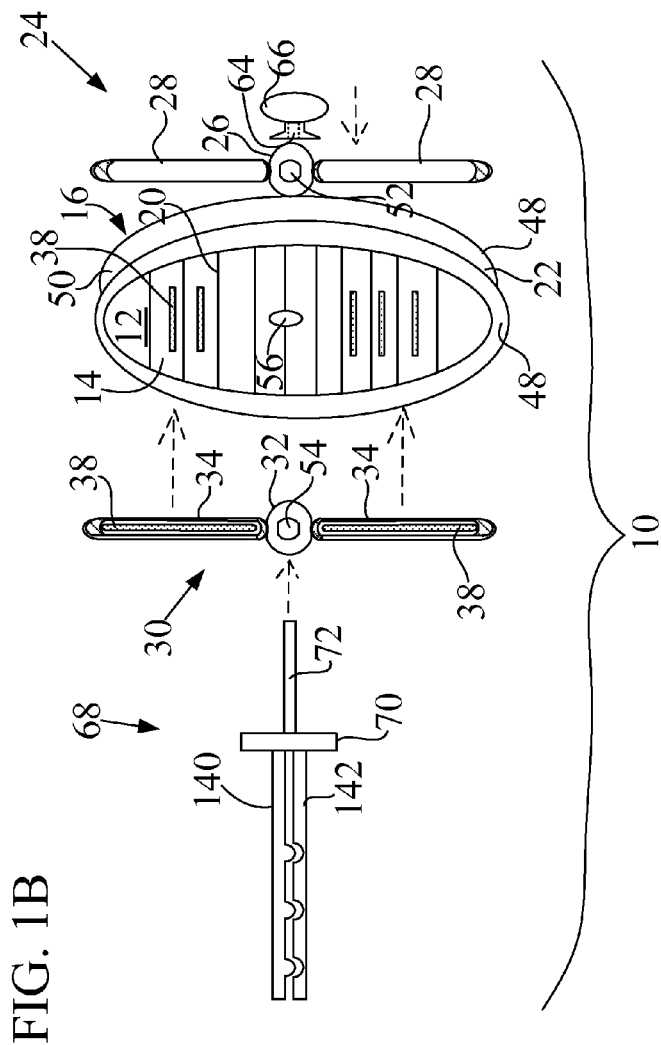
FIG. 1B depicts an exploded schematic assembly view of another embodiment of an air freshening clip cabin air cleaning device, consistent with the present invention.

In the clip means embodiment shown in FIG. 1B, the elongated clip means 36 replaces the rod tensioning member 58 and the rod members 40, 42 with the bifurcated mounting clip 68. The bifurcated mounting clip 68 is preferably a unitary one-piece molded compo net including parallel abutting rod members 140, 142 permanently affixed to a rear side of the backing plate 70. Extending axially outwardly from an opposing front side of the backing plate 70 is a dowel pin 72, The dowel pin 72 in FIG. 1B has an end received into and extending through the support members 24, 30 and captured and secured into the brand circle clip 66 as discussed earlier above with the clip means 36 and FIG. 1A. Other features are generally the same as in FIG. 1A.

In FIG. 1A and 1B a scented air freshening material 38 including volatizing aromatic agents is arranged on or in at least one of the support members 24, 30 or on or in the filter media 12 and/or the annular frame member 22. The air freshening material 38 is preferably a gelatin gel type air freshening composition as is known to those skilled in the art. The air freshening material may be layered onto the support members 24, 30, embedded within the support members 24, 30, applied in stripes or sprayed onto portions of the air filter material 12, or embedded within the air filter material 12. Advantageously, the air freshening agent or material 38 is provided on and volatized from the freshening clip cabin air cleaner 10 without requiring electric heating elements and a supply of electric power as in at least some of the prior art. Additionally, the air freshening agent or material 38 is preferably a gel type material and not a scented liquid which is subject to spilling as in prior art.

The air freshening agent or material 38 is diffused into the airflow stream of the air vent and thereby widely dispersed in the air of the vehicle or room or other surroundings. While the airflow stream is scented by the volatizing aromatic agents of the air freshening material 38, a portion of the air vent airflow is advantageously filtered by the air filter media 12 to remove contaminants and particulates. Contaminants may include not only particulate contaminants but may also include chemical contaminants and allergy agents, for example, pollen.

In at least some embodiments the filter media 12 may additionally be provided with an antimicrobial, antibacterial agent. For example, it is known that metal silver is an effective antibacterial agent. It is also documented that silver-coated fibers are effective antibacterial agents. In at least some embodiments, the filter media 12 may include antimicrobial or antibacterial materials, for example silver coated fibers, to improve the purity of the airflow through the air vent. Other antibacterial agents may also be utilized and arranged on the filter media, such agents as would be known to those skilled in the art and include various formulations of antibacterial agents such as found in antibacterial hand lotions, for example.

The freshening clip cabin air cleaner 10 may be utilized in a variety of environments including filtering and freshening air in automotive air outlet vents, as well as in residential or apartment heating and air conditioning vents, outside air vents such as in wash rooms and a variety of other applications that may benefit from filtered and freshened/scented air but which may lack provisions for installing a filter directly.

Figure 1C:
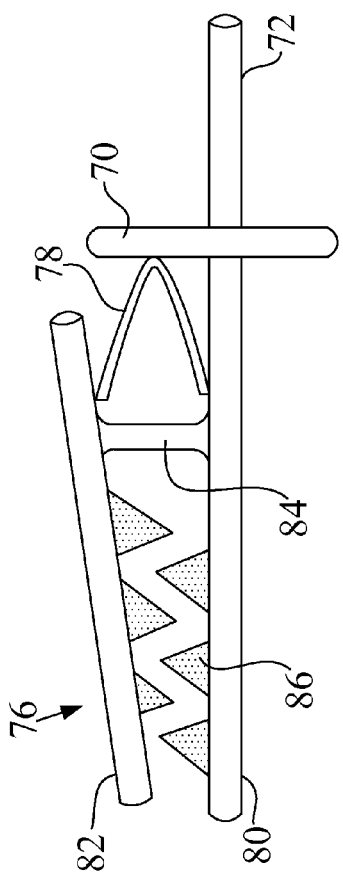
FIG. 1C depicts schematic side view of a variant of the embodiment of FIG. 1B in which the bifurcated mounting clip 68 is replaced with a spring clip.

FIG. 1C depicts a schematic side view of a variant of the embodiment of FIG. 1B. In FIG. 1C the bifurcated mounting clip 68 is replaced with a spring clip 76 which is operable to compressibly clamp onto a vent grill of an air vent. The spring clip 76 has a pair of facing and compressibly engaging jaws 80, 82 which are rotatably secured together pivot about a pivot point 84 relative to each other. The pivot point 84 may be provided by a hinge connection, or preferably by an elastically flexible web 84 as illustrated. Preferably the jaws 80, 82 and web 84 together with the dowl pin 72 are formed as a unitary one-piece plastic molded part, although separate components may alternately be utilized to realize the invention.

The jaws 80, 82 include a plurality of facing and engageable gripping elements 86, formed as teeth or ridged onto facing surfaces of the jaws 80, 82. A spring member 78 is provided to bias or urge the jaws 80, 82 to compressibly mate to capture or mount onto an air vent grill to support the freshening clip cabin air cleaner on the air vent grill. Preferably the spring member 78 is a U-shaped plastic leaf spring member and is a unitary piece formed with together with the spring clip and down pin as part of the unitary molded plastic component. In other embodiment the spring member may be a metal left spring member 78 or utilize a coiled metal spring to bias the jaws as would be know to those skilled in the art. In other variations the spring clip 78 may realized as one or more stamped metal jaw components with a pinned hinge as the pivot point rather than molded plastic jaw components.

Referring now to FIG. 2. FIG. 2 depicts a schematic view of the outlet airflow face 16 of the freshening clip cabin air cleaner 10 of the above Figures, showing the filter media, possibly with pleats 20 and an embodiment of the swept decorative front support member 24, consistent with the present invention. The periphery edges of the elongated wing members 28 of the front support member 24 are preferably bounded by simple or complex arc or conic curves forming a smooth sweeping decorative outline and appearance to the front support member 24. As can be seen in the embodiment of FIG. 2, the wing members 28 extend onto and abut against the spaced legs 48 of the annular frame member 22 surrounding the peripheral filter media edges 18 of the filter media 12.

FIG. 3 depicts an embodiment of the freshening clip cabin air cleaner 10 detachably mounted onto the air vent grill 46, consistent with the present invention. Although the freshening clip cabin air cleaner 10 is illustrated as circular, the freshening clip cabin air cleaner may be advantageously shaped to conform with or match the shape of the air vent grill 46, for example substantially rectangular for a rectangular grill.

In the foregoing specification, specific embodiments of the present invention have been described. However, one of ordinary skill in the art appreciates that various modifications and changes can be made without departing from the scope of the present invention as set forth in the claims below. Accordingly, the specification and figures are to be regarded in an illustrative rather than a restrictive sense, and all such modifications are intended to be included within the scope of the present invention. The benefits, advantages, solutions to problems, and any element(s) that may cause any benefit, advantage, or solution to occur or become more pronounced are not to be construed as a critical, required, or essential features or elements of any or all the claims The invention is defined solely by the appended claims including any amendments made during the pendency of this application and all equivalents of those claims as issued.

The invention claimed is:

1. A freshening clip cabin air cleaner comprising:
    an airflow permeable filter media having peripheral filter media outside edges extending between an inlet airflow face and an outlet airflow face of said media;
    an annular frame member arranged at and extending circumferentially around said peripheral edges of said filter media,
    wherein said filter media is supported by said annular frame;
    at least one support member arranged at and extending over at least a portion of said airflow faces;
    an elongated clip mounting means having a first end mounted to at least one of said at least one support member and extending axially outwardly away from said filter media, said elongated clip means including
        an opposing second end detachably mountably engaged into an air vent grill, mounting said freshening clip cabin air cleaner to said air vent grill;
    a scented air freshening material having volatizing aromatic agents is arranged on or in at least one of said at least one support members, said annular frame member or said filter media,
    wherein said at least one of said annular frame and said at least one support member retain said filter media within said annular frame member,
    wherein said at least one support member includes
        a front support member arranged on said outlet airflow face, said front support member including
        a centrally arranged mounting hub arranged at said outlet airflow face having a hole extending therethrough;
        a plurality of shaped elongated wing members having a first end permanently affixed to said hub and extending radially outwardly from said hub and an opposing second end, said wing members extending across a portion of said outlet face;
    wherein said front support member is a unitary one-piece component,
    wherein said first end of said clip mounting means extends through said hole in said filter media and therefrom through said hole in said front support member.

2. The freshening clip cabin air cleaner according to claim 1, wherein
    said annular frame member is circumferentially closed, said annular frame member encircling and enclosing all of said peripheral outside edges of said filter media.

3. The freshening clip cabin air cleaner according to claim 1, wherein
    said at least one support member is a unitary one-piece component with said annular frame member.

4. The freshening clip cabin air cleaner according to claim 1, wherein said elongated clip means comprises:
    an elongated mounting member including
        a first and a second elongated mounting rod members positioned in a side-by-side substantially parallel arrangement,
    wherein said mounting rod members include a cooperatively engaging retention feature formed onto said mounting rod members, said retention feature configured to detachably mount said air freshening filter to said air vent grill.

5. The freshening clip cabin air cleaner according to claim 1, wherein
    said annular frame member has a generally "U" shaped cross section defined by two spaced legs and a connecting outer wall with a gap between the legs,
    wherein said peripheral filter media edges are received in said gap,
    wherein one of said legs extends inwardly from said peripheral filter media edges to cover an outer portion of said filter media inlet face, and
    wherein another one of said legs extends inwardly from said peripheral filter media edges to cover an outer potion of said filter media outlet face.

6. The freshening clip cabin air cleaner according to claim 1, wherein
    said support members are substantially rigid.

7. The freshening clip cabin air cleaner according to claim 1, wherein
    said wing members extending across said portion of said outlet face abut against said annular frame member.

8. The freshening clip cabin air cleaner according to claim 1, wherein said at least one support member includes
a rear support member arranged on said inlet airflow face, said rear support member including
a centrally arranged mounting hub arranged at said inlet airflow face and having a hole extending therethrough;
a plurality of shaped elongated wing members having a first end permanently affixed to said hub and extending radially outwardly from said hub and an opposing second end, said wing members extending across a portion of said inlet face;
wherein said rear support member is a unitary one-piece component,
wherein said first end of said clip mounting means is received through said hole in said rear support member, extending therefrom through said hole in said filter media,
wherein said annular frame member has a generally "U" shaped cross section defined by two spaced legs and a connecting outer wall with a gap between the legs,
wherein said peripheral filter media edges are received into said gap,
wherein one of said legs extends inwardly from said peripheral filter media edges to cover an outer portion of said filter media inlet face,
wherein another one of said legs extends inwardly from said peripheral filter media edges to cover an outer potion of said filter media outlet face,
wherein said wing members extending across said portion of said outlet face abut against and onto a respective one of said spaced legs of said annular frame member.

9. The freshening clip cabin air cleaner according to claim 1, wherein
said airflow permeable filter media comprises a non-pleated filter mat of synthetic non-woven filter media.

10. The freshening clip cabin air cleaner according to claim 1, wherein
said airflow permeable filter media comprises any of: synthetic non-woven filter media, cellulose based or paper filter media, foam filtering media, woven fabric filter media, and
wherein said airflow permeable filter media is pleated or non-pleated.

11. A freshening clip cabin air cleaner comprising:
an airflow permeable filter media having peripheral filter media outside edges extending between an inlet airflow face and an outlet airflow face of said media;
an annular frame member arranged at and extending circumferentially around said peripheral edges of said filter media,
wherein said filter media is supported by said annular frame;
at least one support member arranged at and extending over at least a portion of said airflow faces;
an elongated clip mounting means having a first end mounted to at least one of said at least one support member and extending axially outwardly away from said filter media, said elongated clip means including
an opposing second end detachably mountably engaged into an air vent grill, mounting said freshening clip cabin air cleaner to said air vent grill;
a scented air freshening material having volatizing aromatic agents is arranged on or in at least one of said at least one support members, said annular frame member or said filter media,
wherein said at least one of said annular frame and said at least one support member retain said filter media within said annular frame member,
wherein said at least one support member includes
a rear support member arranged on said inlet airflow face, said rear support member including
a centrally arranged mounting hub arranged at said inlet airflow face and having a hole extending therethrough;
a plurality of shaped elongated wing members having a first end permanently affixed to said hub and extending radially outwardly from said hub and an opposing second end, said wing members extending across a portion of said inlet face;
wherein said rear support member is a unitary one-piece component,
wherein said first end of said clip mounting means is received through said hole in said rear support member, extending therefrom through said hole in said filter media.

12. A freshening clip cabin air cleaner comprising:
an airflow permeable filter media having peripheral filter media outside edges extending between an inlet airflow face and an outlet airflow face of said media;
an annular frame member arranged at and extending circumferentially around said peripheral edges of said filter media,
wherein said filter media is supported by said annular frame;
at least one support member arranged at and extending over at least a portion of said airflow faces;
an elongated clip mounting means having a first end mounted to at least one of said at least one support member and extending axially outwardly away from said filter media, said elongated clip means including
an opposing second end detachably mountably engaged into an air vent grill, mounting said freshening clip cabin air cleaner to said air vent grill;
a scented air freshening material having volatizing aromatic agents is arranged on or in at least one of said at least one support members, said annular frame member or said filter media,
wherein said at least one of said annular frame and said at least one support member retain said filter media within said annular frame member,
wherein said elongated mounting means includes
an stiff elongated mounting member having
a first end detachably and supportively secured to said filter media and/or said annular frame;
an opposing second end having a first jaw member;
a second jaw member pivotably secured to said elongated mounting member;
a flexible web connecting said first and second jaws, said flexible web forming a pivot point for said jaws;
wherein said first and second jaws include engaging gripping elements for detachably mount said air freshening filter to said air vent grill;
wherein said first and said jaws are biased to facing close by a spring element acting upon jaws,
wherein said spring member is any of: a coil spring, a U-shaped leaf spring.

13. The freshening clip cabin air cleaner according to claim 12, wherein
said spring member is any of: a coil spring, a U-shaped leaf spring.

14. The freshening clip cabin air cleaner according to claim 13, wherein
said elongated mounting member including said jaws and web is a unitary one-piece molded plastic part.

15. The freshening clip cabin air cleaner according to claim 12, wherein
said annular frame member is circumferentially closed, said annular frame member encircling and enclosing all of said peripheral outside edges of said filter media.

16. The freshening clip cabin air cleaner according to claim 12, wherein
said airflow permeable filter media comprises a non-pleated filter mat of synthetic non-woven filter media.

17. The freshening clip cabin air cleaner according to claim 12, wherein
said airflow permeable filter media comprises any of: synthetic non-woven filter media, cellulose based or paper filter media, foam filtering media, woven fabric filter media, and
wherein said airflow permeable filter media is pleated or non-pleated.

* * * * *